United States Patent
Mondello

(10) Patent No.: US 9,067,167 B2
(45) Date of Patent: Jun. 30, 2015

(54) METHOD AND INSTRUMENTATION FOR COMPREHENSIVE MULTIDIMENSIONAL CHROMATOGRAPHY SEPARATIONS USING A MICRO FLOW MODULATOR

(76) Inventor: Luigi Mondello, Vill. Ganzirri (IT)

(*) Notice: Subject to any disclaimer, the term of this patent is extended or adjusted under 35 U.S.C. 154(b) by 82 days.

(21) Appl. No.: 13/699,068

(22) PCT Filed: May 24, 2011

(86) PCT No.: PCT/EP2011/058404
§ 371 (c)(1),
(2), (4) Date: Nov. 20, 2012

(87) PCT Pub. No.: WO2011/147801
PCT Pub. Date: Dec. 1, 2011

(65) Prior Publication Data
US 2013/0068100 A1    Mar. 21, 2013

(30) Foreign Application Priority Data
May 27, 2010 (IT) .............................. ME2010A0011

(51) Int. Cl.
*B01D 53/02* (2006.01)
*G01N 30/60* (2006.01)
(Continued)

(52) U.S. Cl.
CPC ............ *B01D 53/02* (2013.01); *G01N 30/6039* (2013.01); *G01N 2030/201* (2013.01); *G01N 30/6034* (2013.01); *G01N 30/32* (2013.01);
(Continued)

(58) Field of Classification Search
CPC . G01N 30/463; G01N 30/465; G01N 30/466; G01N 30/6034; G01N 30/6039; G01N 30/6043; G01N 30/7206; G01N 2030/201

USPC ................. 73/23.42; 95/86; 96/101, 104, 106
See application file for complete search history.

(56) References Cited

U.S. PATENT DOCUMENTS 6,730,228 B2 * 5/2004 Petro et al. ...................... 506/12
6,998,095 B2 * 2/2006 Anderson et al. ............. 422/539
(Continued)

OTHER PUBLICATIONS

Tranchida, P. Q. et al: "Optimized use of a 50 [mu]m internal diameter secondary column in a comprehensive two-dimensional gas chromatography system", Analytical Chemistry, vol. 81, No. 20, Oct. 15, 2009, pp. 8529-8537.*
(Continued)

*Primary Examiner* — Robert Clemente
(74) *Attorney, Agent, or Firm* — Silvia Salvadori, P.C.

(57) ABSTRACT

The present invention refers to a modulator, to be used for comprehensive multidimensional chromatography separations, to entrap and release sample solute fractions (entrapped in a capillary loop of fixed or variable volume), deriving from a capillary column with an internal diameter ranging from 0.01 mm to 0.53 mm, onto another capillary column with an internal diameter ranging from 0.01 mm to 0.53 mm. The micro-device has been integrated in a gas chromatographic system, composed of two ovens for the independent temperature control of the two columns; the micro-device is characterized, internally, by a system of channels that enable the controlled splitting of gas flow, entering the second capillary, to generate an optimum gas linear velocity and to release the pressure in excess, with the objective of attaining the maximum separation efficiency in the second column. Furthermore, the system is equipped with a second device, to divide the flow exiting the second column in two different detectors that operate at the same or at different pressures.

12 Claims, 4 Drawing Sheets

(51) Int. Cl.
*G01N 30/32* (2006.01)
*G01N 30/46* (2006.01)
*G01N 30/20* (2006.01)
*G01N 30/72* (2006.01)
*G01N 30/30* (2006.01)

(52) U.S. Cl.
CPC ............ *G01N 30/463* (2013.01); *G01N 30/465* (2013.01); *G01N 30/7206* (2013.01); *G01N 2030/3084* (2013.01); *G01N 2030/324* (2013.01)

(56) References Cited

U.S. PATENT DOCUMENTS

| | | | | |
|---|---|---|---|---|
| 7,451,634 | B2* | 11/2008 | Gamache et al. | 73/23.42 |
| 7,518,103 | B2 | 4/2009 | Amirav | |
| 8,104,513 | B2* | 1/2012 | Furukawa | 137/806 |
| 8,303,694 | B2* | 11/2012 | Tipler | 96/101 |
| 8,562,837 | B2* | 10/2013 | Tipler | 210/656 |
| 8,603,833 | B2* | 12/2013 | Malik et al. | 436/178 |
| 8,721,768 | B2* | 5/2014 | Tipler | 95/82 |
| 2004/0232366 | A1 | 11/2004 | Seeley | |
| 2010/0101411 | A1 | 4/2010 | Tipler | |
| 2011/0185797 | A1* | 8/2011 | Sakai et al. | 73/61.56 |

OTHER PUBLICATIONS

Poliak, et al: "Pulsed flow modulation comprehensive two-dimensional gas chromatography", Journal of Chromatography, vol. 1186, No. 1-2, Mar. 13, 2008, pp. 189-195.*

Micyus, N.J., et al: "Analysis of aromatic compounds in gasoline with flow-switching comprehensive tow-dimensional gas chromatography", Journal of Chromatography, vol. 1086, No. 1-2, Sep. 9, 2005, pp. 115-121.*

Kochman, M., et al: "Flow modulation comprehensive two-dimensional gas chromatography-mass spectrometry with a supersonic molecular beam", Journal of Chromatography, vol. 1129, No. 1, Sep. 29, 2006, pp. 95-104.*

Trnachida, P. Q., et al: "Generation of improved gas linear velocities in a comprehensive two-dimensional gas chromatography system", Analytical Chemistry, vol. 79, No. 6, Mar. 1, 2007, pp. 2266-2275.*

Trnachida, P. Q., et al: "A flexible loop-type flow modulator for comprehensive two-dimensional gas chromatography system", Journal of Chromatography, vol. 1218, No. 21, May 1, 2011, pp. 3140-3145.*

Tranchida, P. Q. et al: "Optimized use of a 50 [mu]m internal diameter secondary column in a comprehensive two-dimensional gas chromatography system", Analytical Chemistry, vol. 81, No. 20, Oct. 15, 2009, pp. 8529-8537, XP002604569, American Chemical Society.

Poliak, et al: "Pulsed flow modulation comprehensive two-dimensional gas chromatography", Journal of Chromatography, Elsevier Science Publishers B.V, NL LNKDDOI: 10.1016/J.Chroma.2007.09.030, vol. 1186, No. 1-2, Mar. 13, 2008, pp. 189-195.

Micyus, N. J., et al: "Analysis of aromatic compounds in gasoline with flow-switching comprehensive two-dimensional gas chromatography", Journal of Chromatography, Elsevier Science Publishers B.V, NL LNKDDOI: 10.1016/J.Chroma.2005.06.015, vol. 1086, No. 1-2, Sep. 9, 2005, pp. 115-121.

Kochman, M., et al: "Flow modulation comprehensive two-dimensional gas chromatography-mass spectrometry with a supersonic molecular beam", Journal of Chromatography, Elsevier Science Publishers B.V, NL LNKDDOI: 10.1016/J.Chroma.2006.06.079, vol. 1129, No. 1, Sep. 29, 2006, pp. 95-104.

Tranchida, P. Q., et al: "Generation of improved gas linear velocities in a comprehensive two-dimensional gas chromatography system", Analytical Chemistry, vol. 79, No. 6, Mar. 1, 2007, pp. 2266-2275.

Tranchida, P. Q., et al: "A flexible loop-type flow modulator for comprehensive two-dimensional gas chromatography", Journal of Chromatography A, vol. 1218, No. 21, May 1, 2011, pp. 3140-3145.

* cited by examiner

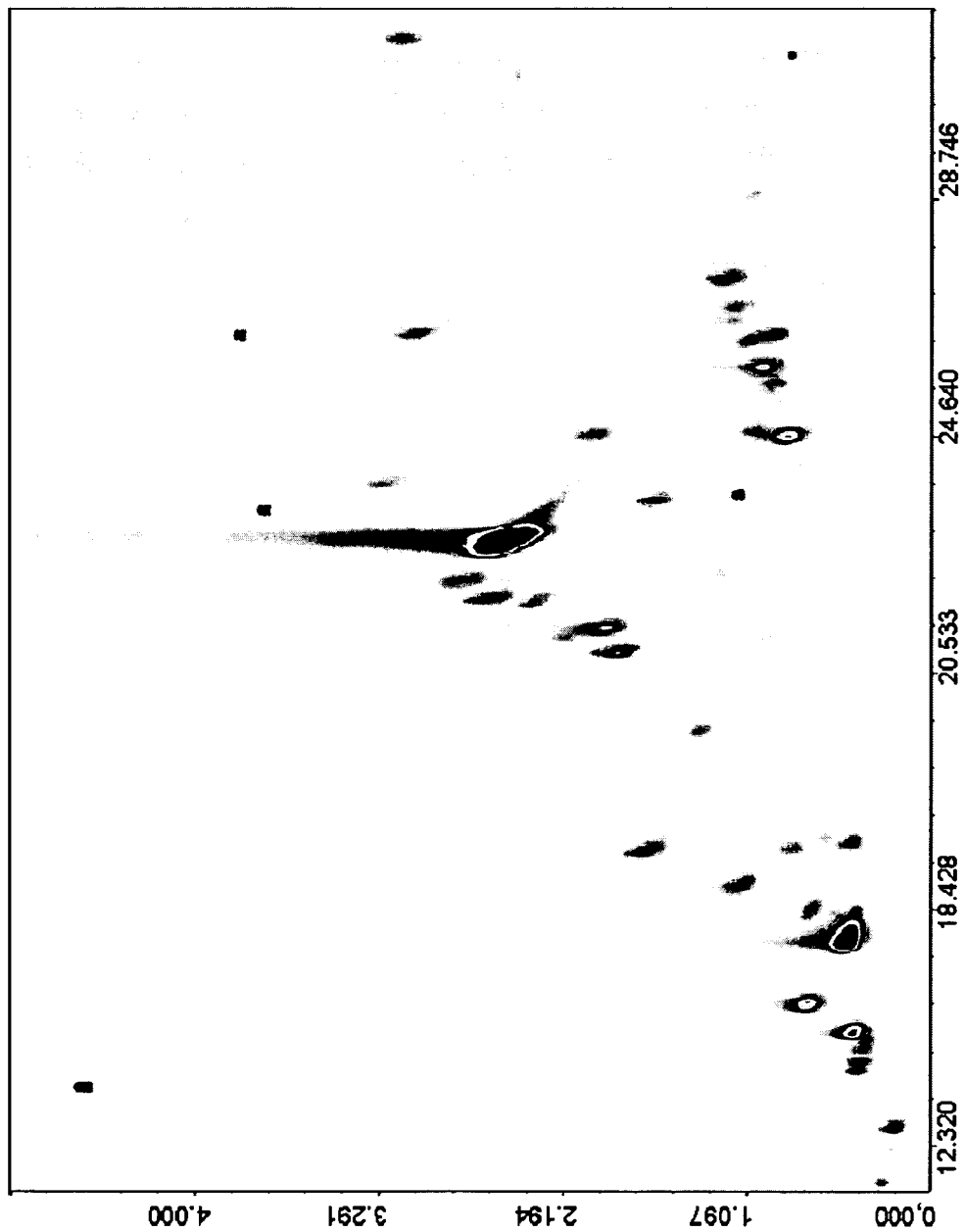

METHOD AND INSTRUMENTATION FOR COMPREHENSIVE MULTIDIMENSIONAL CHROMATOGRAPHY SEPARATIONS USING A MICRO FLOW MODULATOR

CROSS-REFERENCE TO RELATED APPLICATIONS

This application is a 371 of PCT/EP2011/058404, filed May 24, 2011, which claims the benefit of priority from Italian Patent Application No. ME2010A000011, filed May 27, 2010, the contents of each of which are incorporated herein by reference.

The present invention refers to a modulator, to be used for comprehensive multidimensional chromatography separations, to entrap and release sample solute fractions (entrapped in a capillary loop of fixed or variable volume), deriving from a capillary column with an internal diameter ranging from 0.01 mm to 0.53 mm, onto another capillary column with an internal diameter ranging from 0.01 mm to 0.53 mm. The micro-device has been integrated in a gas chromatographic system, composed of two ovens for the independent temperature control of the two columns; the micro-device is characterized, internally, by a system of channels that enable the controlled splitting of gas flow, entering the second capillary, to generate an optimum gas linear velocity and to release the pressure in excess, with the objective of attaining the maximum separation efficiency in the second column. Furthermore, the system is equipped with a second device, to divide the flow exiting the second column in two different detectors that operate at the same or at different pressures. Gas chromatography (GC) is generally achieved through the use of a capillary column for the separation of the constituents of a mixture. Comprehensive multidimensional gas chromatography (GC×GC) is certainly the most revolutionary and innovative technique in the gas chromatography field. In an ideal comprehensive multidimensional gas chromatography system the peak capacity is equal to the product of the two single peak capacities ($n_1 \times n_2$) in the two dimensions. Although such a value is optimistic, the peak capacity generated by GC×GC systems is certainly unprecedented and is particularly suitable for the separation of complex mixtures of volatiles, prior to the detection system. The advantages of these methods, compared to conventional ones (one-dimensional) are mainly three:

increased separation power enhanced sensitivity formation of two-dimensional chromatograms with regions occupied by chemically-similar compounds. This aspect is particularly important for the identification of unknown compounds, in the absence of mass spectral libraries or when mass spectra are very similar (for example, homologous series of compounds such as fatty acids, terpenes, etc.).

Amongst all comprehensive multidimensional chromatography methods, GC×GC has been probably the most applied and developed. A GC×GC separation is normally obtained on two capillary columns, linked in series, and with a transfer device, defined as modulator, positioned between the two columns. The function of the modulator is to isolate, re-concentrate and introduce fractions of effluent from the primary column onto the secondary capillary column, continuously throughout the analysis. The time required to complete this process is defined as the modulation period (generally between 1 and 10 seconds). The primary column is generally apolar and, hence, the separation is based on the boiling-point differences (not only on these) between the different analytes. Each modulation generates fractions which undergo a further rapid separation on the second column, generally of polar chemistry: isovolatile compounds are resolved on the basis of polarity-based interactions (dipole-dipole, hydrogen bond, polarization effects).

GC×GC was introduced in 1991 by John B. Phillips and Zaiyou Liu (Z. Lui et al. J. Chromatogr. Sci. 29, 227, 1991, U.S. Pat. No. 5,135,549 Ago. 9, 1992) using a thermal modulator. Later, other modulators were introduced which used cryogenic fluids, mainly (R. M. Kinghorn et al. J. High Resolut. Chromatogr. 21, 620, 1998; E. B. Ledford et al. J. High Resolut. Chromatogr. 23, 202, 2000; J. Beens et al. J Chromatogr. A 919, 127 2001, U.S. Pat. No. 6,838,288 B2, Jan. 5, 2005; and M. Adahchour et al. Analyst 128, 213 2003, US Patent Application 2005/0106743 A1 May 19, 2005). The modulators above reported, require cryogenic fluids and adequate devices to introduce the cryogenic fluids into the gas chromatographic oven. In the last decade, modulators using cryogenic fluids, such as $CO_2$ and $N_2$, have gained increasing popularity. However, it needs to be emphasized that the use of cryogenic fluids is rather expensive, considering the quantities employed. Consequently, the development of cryogen-free GC×GC techniques has always generated interest in various research groups.

The first pneumatic modulator for GC×GC, with no need for cryogenic fluids, was described by Bruckner et al. Anal. Chem. 70, 2796 1998, and later modified by J. Seeley (J. V. Seeley, et al. Anal. Chem. 72, 4346 2000; U.S. Pat. No. 6,632,268 Feb. 4, 2002).

The latter system is based on the employment of a 6-port valve, located between the first and second dimension. Two stages characterize the modulation process: a first accumulation stage, during which a chromatography band from the first dimension is accumulated in a sample loop, followed by a re-injection stage, during which the band is introduced onto the head of the second column, through a high gas flow. The valve is held in the accumulation position for about 80% of the modulation period, and the remaining 20% of time is used for re-injection; during the latter period the primary column effluent is directed to waste. Using such a configuration, the primary column chromatography bands are compressed in time, more than space. The analysis time in the second dimension is very rapid and under non-optimum conditions for a fast analysis. A further drawback is related to the position of the diaphragm valve inside the oven, limiting the use of a chromatography column to the maximum valve operational temperature. Other experiments were carried out using pneumatic modulators with improved temperature limits (for example by locating the head of the valve inside the oven and leaving the remaining parts outside). Later, other cryogen-free GC×GC approaches, using another pneumatic modulator system, were studied by the same author (Bueno P. A. et al. J. Chromatogr. A 1027, 3, 2004, U.S. Pat. No. 7,247,189 B2 Jul. 24, 2007). The modulator contains two sampling loops, connecting via two metallic branches to a 3-way solenoid valve, that receives an auxiliary gas, through an electronic pressure control system. One of the two sample loops is filled with effluent from the first column when the solenoid valve in the collecting stage; the time required to fill the loop is generally less than 2 sec., and this is dependent on the primary column gas flow. At the end of the collecting stage, the loop is emptied using a high gas flow (circa 20 mL/min.), switching the solenoid to the re-injection phase, the duration of which is about 0.1 sec. This collection and re-injection stage occurs in an alternate mode in each loop.

In conventional GC×GC experiments, first and second-dimension capillaries are always operated under compromise gas-flow conditions, namely nearly ideal in the primary column and much too high in the second. Such a negative aspect was circumvented by Tranchida P. Q. et al. in 2009 (Analytical Chemistry, vol. 81(20), 2009, pages 8529-8537). The authors describe a cryogenically-modulated GC×GC system consisting of an apolar 30 m×0.25 mm i.d. column linked, by means of a T-union, to a flame ionization detector-connected high-resolution 1 m×0.05 mm i.d. polar one and to a 0.20 m×0.05 mm i.d. uncoated capillary segment; the latter is connected to a manually operated split valve, located on top of the second GC. The generation of optimum gas linear velocities in both dimensions is attained by regulation of the needle valve, hence splitting gas flows at the outlet of the first dimension.

BRIEF DESCRIPTION OF THE DRAWINGS

FIGS. 2A and 3A show a detail of FIG. 1 while valve 8 is in the "normally-closed" position.

FIGS. 2B and 3B show a detail of FIG. 1 while valve 8 is in the "normally-opened" position.

FIG. 6 shows the separation of a mint essential oil attained with a flame ionization detector.

SUMMARY OF THE INVENTION

Figure 1:
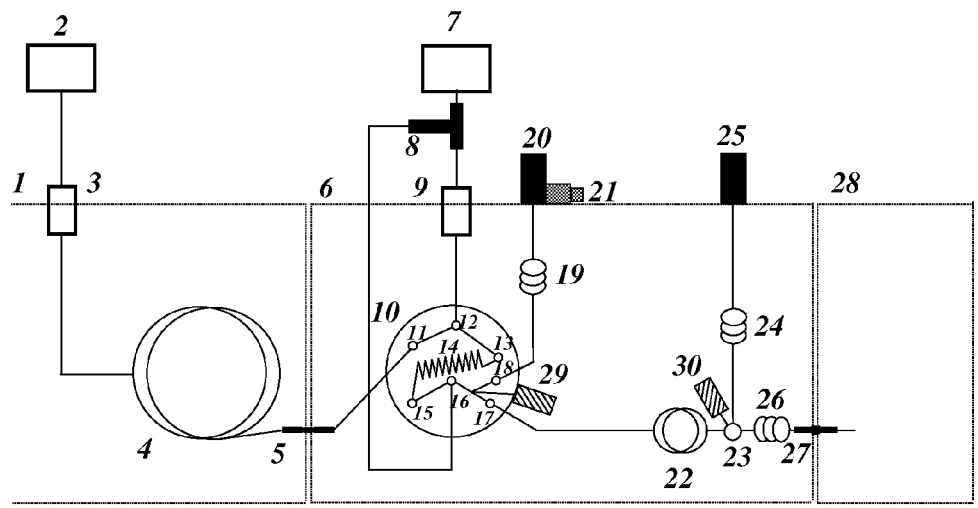
FIGS. 1 and 2 show a modulator for comprehensive multidimensional chromatography for samples collected in a capillary loop of variable volume.

The present invention relates to a device that functions as modulator used in chromatography, and in particular, in comprehensive multidimensional chromatography, comprising:
  a port that receives effluent from a chromatography column;
  one or two external capillary sample loops, or one or two sample loops integrated in the modulation device;
  two independent ports that receive a flow from one or more electronic pressure and/or flow control devices;
  three channels, either integrated, or located externally with respect to the modulation device, to split, in a controlled manner, the flow exiting the sample loop and to release the pressure in excess within the device and into the second column with a different objective with respect to the system introduced by Tranchida et al (Analytical Chemistry, vol. 81(20), 2009, pages 8529-8537) where the aim of the split-flow device was only to reduce the linear velocity in the second dimension.
  a needle valve, either integrated or external to the device, that regulates the flow exiting the accumulation capillary;
  a system of integrated channels that connects the different ports in an appropriate manner.

In a preferred embodiment, said one or two external capillary sample loops, easy to interchange and to vary the accumulation volume, are characterized by a ratio between capillary length and internal diameter within 5 and 40, to avoid the re-mixing of components separated in the first dimension.

The device, object of the present invention, can comprise one or two internally integrated accumulation channels, with a fixed volume.

In the system of integrated channels of the device according to the present invention, the internal connection channels can be arranged in groups and in a discontinuous manner; these groups can be connected to one another via one or two external accumulation capillaries.

Alternatively, the internal connection channels can be arranged in a continuous manner, via an internal accumulation channel.

The device object of the present invention enables the division of the flow exiting the accumulation capillary, through channels integrated in the modulation device, or, in any case, positioned before the second separative capillary column.

In a further embodiment of the present invention, the device can be connected to a micro needle valve, either integrated or external to the modulation device, the regulation of which enables the division of the flow and the release of the pressure in excess deriving from the modulation re-injection step. In the case of the external valve, regulation is achieved using the needle valve, under constant flow splitting conditions, or under non-constant flow splitting conditions, by using a solenoid valve connected in series to the needle valve. In the case of the integrated needle valve in the device, the two-way solenoid valve is located outside the gas chromatography oven.

When the device according to the present invention is connected to two separation columns of equal dimensions, the two detectors operate at equal pressures, when the device according to the present invention is connected to two separation columns of different dimensions, the two detectors operate at different operational pressures.

The device of the present invention can have the two chromatography columns installed in one or more gas chromatography ovens. In the case the twin-oven configuration is employed, combined with the flow splitting device, higher or lower secondary oven temperatures can be applied to increase or reduce the separation velocity in the second dimension, respectively.

The injector directly linked to the modulation device is connected to a controller which can be an automatic flow controller or an automatic pressure controller.

The device object of the present invention can be used in a GC×GC method comprising a mass spectrometer at the outlet of the second column, or any other GC detector.

The device object of the present invention can be used also in conventional gas chromatography, and used as rapid high-pressure injection system, of samples vaporized inside the injector, linked directly to the modulation device; the latter is characterized by an appropriate accumulation loop, with a volume equal or greater of that of the vapour generated from the injected volume. The inlet port of the first dimension column, of the modulator device, must be closed if used in the rapid high-pressure injection configuration.

The device according to the present invention can be employed with any type of fluid, and, hence, also with packed columns with an internal diameter from 1 mm to 6 mm.

DETAILED DESCRIPTION OF THE INVENTION

Figure 2:
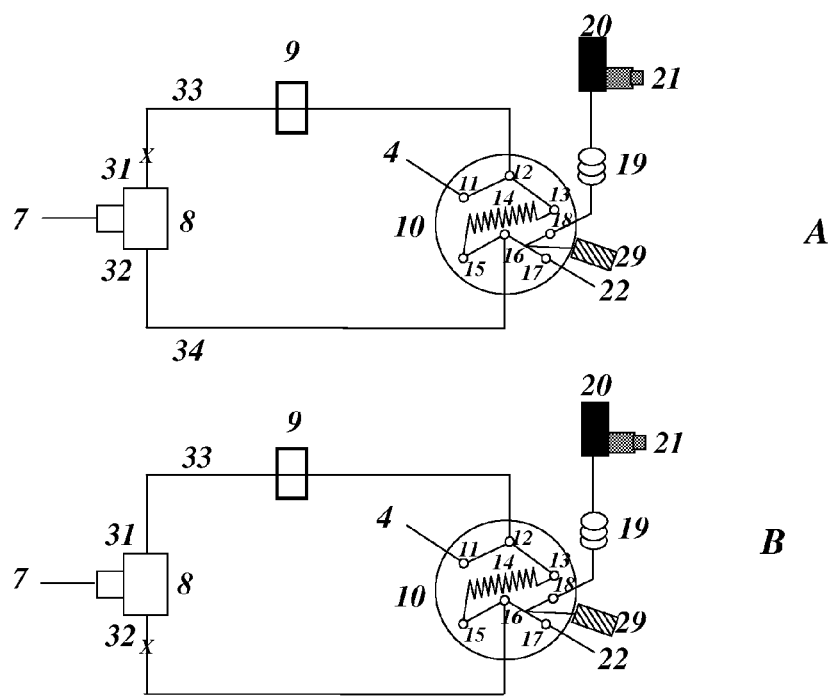
Figure 3:
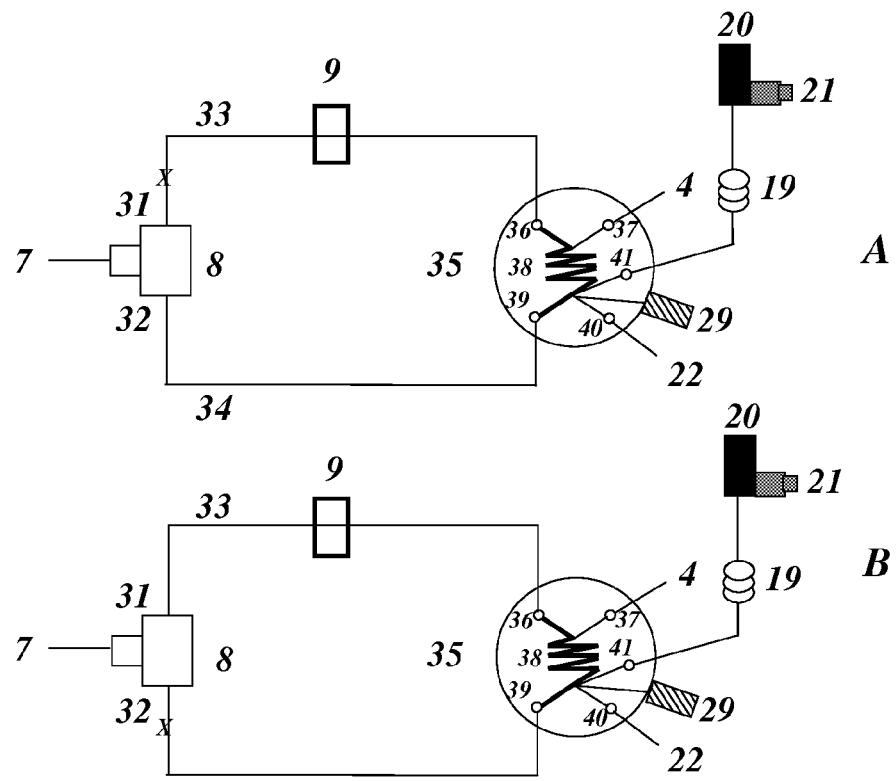
FIG. 3 shows a modulator for comprehensive multidimensional chromatography for samples collected in a capillary loop of fixed volume.

The modulator for comprehensive multidimensional chromatography (GC×GC) is illustrated in FIG. 1-3, according to the present invention. Briefly, the modulator entraps and releases solute fractions of a sample (collected in a capillary loop of variable (FIG. 1,2) or fixed volume (FIG. 3)), deriving from a capillary column with an internal diameter ranging from 0.01 mm to 0.53 mm, onto another capillary column with an internal diameter ranging from 0.01 mm to 0.53 mm.

The micro-device has been integrated in a gas chromatographic system, composed of two ovens for the independent temperature control of the two columns; the micro-device is characterized, internally, by a system of channels (FIG. 1-3) that enable the controlled splitting of gas flow, entering the second capillary, to generate an optimum gas linear velocity and to release the pressure in excess, with the objective of attaining the maximum separation efficiency in the second column. Furthermore, the system is equipped with a second device, to divide the flow exiting the second column in two different detectors that operate at the same or at different pressures.

Figure 4:
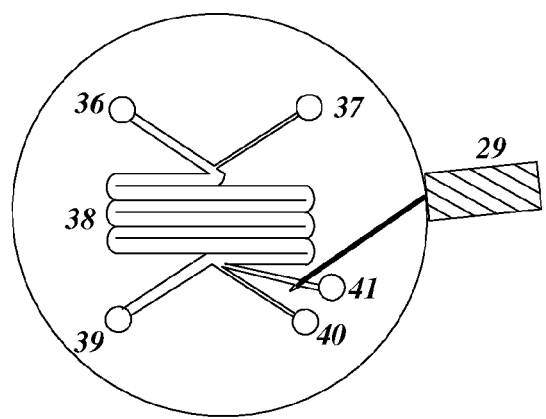
FIG. 4 shows an enlargement of the modulator for comprehensive multidimensional chromatography.

In reference to FIG. 1, the systems comprise two gas chromatography ovens 1,6, two automatic pressure regulators 2,7, two injectors 3,9, two separative capillary columns 4,22, that are linked to the modulator 10, a detector 28 that operates at ambient pressure or at any other pressure. Device 20 can consist, alternatively, of a detector or of a needle valve, that can be connected to a two-position solenoid valve (21), using capillary 19 as a separation or deactivated column, respectively. At the end of the second column (22), a second device (23), regulated by using a needle valve (30), enables flow division in two different capillaries (24,26), linked to two detectors (25,28) that operate at equal or different pressures. Additionally, a particularly important aspect is represented by the flow splitting, of the effluent collected in the accumulation capillary loop 14, that enables the optimization of the secondary-column linear velocity (22) and the release of the pressure in excess, when the loop is emptied through a pressure increase, which is generated by switching the 3-way valve 8. Flow splitting is obtained through channels, internally-located in device 10, connected to two capillaries characterized by a different length and/or diameter (one represented by column 22 and the other by a capillary 19, connected to device 20,21). Flow splitting can be regulated by a needle valve (29) integrated in device 10; in the latter situation, device 20 works as a detector (in such a configuration, device 21 is not present). The function of needle valve 29 can be substituted by device 20, which, in such a case, is not a detector but a needle valve. Briefly, the system enables the introduction of a mixture of compounds, through injector 3 and onto column 4, where the first separation occurs at the independent temperature of gas chromatograph 1. The compounds are transferred to the second gas chromatograph (6), location of the modulator, through a heated transfer line (5), which is held at an adequate temperature. A scheme of the modulator, with an integrated internal loop (38), is reported in FIG. 3. In this case, the modulation mechanism of device 35 is equivalent to that previously described (10), with the exception of the number of ports. An enlargement of device 35 is illustrated in FIG. 4, emphasizing the introduction point of the needle valve (29).

Briefly, the compounds separated on capillary column 4, enter modulator 10 (or 35) through port 11 (or 37), after leaving the first gas chromatography, through the transfer line (5). Modulation is divided in two stages, illustrated in FIGS. 2,3 A and B. In detail, the components are accumulated in the modulator communicating channels 11-12-13, located internally, and in the sample loop 14 (or internal loop 38, through the channel connecting 37 to 38), for a variable period between 1-10 seconds, pushed by the flow deriving from device 2, while valve 8 is in the "normally-closed" position (31) and in the "normally-opened" position (32), that is, with a gas flow in branch 34 (FIG. 2A,3A), that is connected to the modulation device via port 16 (or 39). At the end of the accumulation stage, valve 8 is switched to position 32, that is, with a gas flow in branch 33, enabling the flushing of capillary 14 (or internal loop 38), through the internal channels 12-13 and 15-16-17/18 (or 36-38-40/41) (FIG. 2B,3B). The duration of the flushing stage is variable, namely between 0.1 and 1 second. At the end of the flushing step, valve 8 is switched, enabling a new accumulation step in capillary 14 (or internal loop 38), and, at the same time, enabling a rapid separation on column 22 and/or 19 and elution of the effluent into devices 20, 25 and 28. The characterizing feature of the invention is represented by the split-flow channels, located internally in the device, namely 16-17 and 16-18 (or 38-40 and 38-41), regulating the integrated needle valve (29) appropriately, in the case device 20 is employed as detector. In the case device 20 is a needle valve, flow splitting is dependent on valve regulation. Such a procedure is of the highest importance, because it enables the optimization of the linear velocity in the second column (22) and, above all, to release the pressure in excess in branch 16-17 (or 38-40) and, consequently, in column 22. In this case, the two-position (open/closed) solenoid valve (21) can be used. During the flushing of capillary 14 (or 38), valve 21 can be left open, or in the closed position, enabling the complete passage of the compounds eluting from the primary column, that are transferred to the second column (22). At this point, solenoid valve 21 is opened for all the duration of the second-dimension analysis, enabling the release of the pressure in excess.

Once achieved the separation in the second column, microdevice 23, equipped with needle valve 30, enables the splitting of the secondary-column (22) effluent, by using two capillaries 24 and 26, of adequate dimensions, between two detectors (25 and 28), operated at equal or at different pressures.

Figure 5:
FIG. 5 shows the separation of a mint essential oil attained with a quadrupole mass spectrometer.

A typical separation attained using the system reported in FIG. 1, object of the invention, is illustrated in FIGS. 5 and 6. In particular, FIG. 5 shows the separation of a mint essential oil, attained with a quadrupole mass spectrometer, while FIG. 6 shows the separation of the same sample with a flame ionization detector. The two bidimensional chromatograms were obtained simultaneously, using the following experimental conditions:

first dimension column (4): 20 m×0.1 mm i.d.×0.1 µm film thickness (chiral);
temperature program: 50-200° C. at 5° C./min;
second dimension column (22): 2.5 m×0.1 mm i.d.×0.1 µm film thickness (polar);
temperature program: 50 (3 min)-200° C. at 5° C./min;
capillary (19): 0.1 m×0.1 mm i.d.;
capillary (24): 0.5 m×0.1 mm i.d.;
capillary (26): 1 m×0.1 mm i.d.;
sample loop (14): 0.1 m×0.51 mm i.d.;
automatic flow controller (2), constant linear velocity: 751 kPa;
automatic flow controller (7), constant linear velocity: 620 kPa;
injected volume: 3 µL;
split ratio: 10:1.
Mass spectrometer interface temperature (27): 250° C.;
mass spectrometer sampling frequency (28): 25 Hz;
flame ionization detector sampling frequency (25): 125 Hz.
Modulation period: 5.5 seconds, of which 5.3 seconds for accumulation+0.2 seconds for re-injection.

The invention claimed is:
1. A device for chromatography comprising:
a modulator
a port that receives effluent from a first chromatographic column;

either one or two capillary sample loops located externally with respect to said modulator or either one or two capillary sample loops integrated in said modulator;

two independent ports of the modulator that receive a flow from one or more electronic pressure and/or flow control devices located externally with respect to said modulator;

three channels either integrated or located externally with respect to said modulator connected to said one or two capillary sample loops and a second column to split with a needle valve the flow exiting an accumulation capillary loop and to release the pressure in excess within the channels connected to said accumulation capillary loop and in the second column when emptying said accumulation capillary loop;

a needle valve, either integrated or external to the modulator that regulates the flow exiting said accumulation capillary loop; and a system of integrated communicating channels that connect different ports, wherein said communicating channels are located internally to the modulator and are connected to one another via said accumulation capillary sample loop and said communicating channels are connected to said second column and to a capillary column.

2. A device, according to claim 1, comprising one or two capillary sample loops located externally with respect to modulator, characterized by a ratio between capillary length and internal diameter within 5 and 40.

3. A device according to claim 1, further comprises a second accumulation capillary with a fixed volume.

4. A device, according to claim 1, wherein in the system of integrated communicating channels, the communicating channels are arranged in groups and in a discontinuous manner and these groups are connected to one another via one or two accumulation capillaries located externally with respect to the modulator.

5. A device, according to claim 1, wherein in the system of communicating integrated channels, the communicating channels are arranged in a continuous manner, via an accumulation capillary loop located internally to modulator.

6. A device according to claim 1, wherein the channels splitting the flow exiting the accumulation capillary are integrated in the device, or positioned before the second separative capillary column.

7. A device, according to claim 4, connected to a micro needle valve, either integrated or external to the modulation device the regulation of which enables the division of the flow and the release of the pressure in excess deriving from a modulation re-injection step.

8. A device, according to claim 4, connected to two separation columns of equal dimensions connected to two detectors that operate at equal pressures.

9. A device, according to claim 4, connected to two separation columns of different dimensions connected to two detectors that operate at different operational pressures.

10. A device, according to claim 1, wherein the two chromatography columns are installed in one or more gas chromatography ovens.

11. A device, according to claim 1, wherein an injector is directly linked to the device.

12. A device, according to claim 11, wherein the injector is connected to an automatic flow controller or to an automatic pressure controller.

* * * * *